United States Patent
Geimer

(10) Patent No.: US 9,018,168 B2
(45) Date of Patent: Apr. 28, 2015

(54) THERAPEUTIC METHOD FOR TREATING CONGESTIVE HEART FAILURE

(75) Inventor: Thomas Robert Geimer, Mount Barker (AU)

(73) Assignee: Madeleine Pharmaceuticals Pty Ltd (AU)

( * ) Notice: Subject to any disclaimer, the term of this patent is extended or adjusted under 35 U.S.C. 154(b) by 0 days.

(21) Appl. No.: 14/000,789

(22) PCT Filed: Aug. 11, 2011

(86) PCT No.: PCT/AU2011/001026
§ 371 (c)(1),
(2), (4) Date: Aug. 21, 2013

(87) PCT Pub. No.: WO2012/019237
PCT Pub. Date: Feb. 16, 2012

(65) Prior Publication Data
US 2013/0324472 A1    Dec. 5, 2013

Related U.S. Application Data

(60) Provisional application No. 61/445,826, filed on Feb. 23, 2011, provisional application No. 61/445,814, filed on Feb. 23, 2011.

(30) Foreign Application Priority Data

Aug. 12, 2010    (AU) ................................ 2010903613

(51) Int. Cl.
*A61K 38/17*    (2006.01)
*A61K 38/22*    (2006.01)

(52) U.S. Cl.
CPC ......... *A61K 38/1709* (2013.01); *A61K 38/2242* (2013.01)

(58) Field of Classification Search
None
See application file for complete search history.

(56) References Cited

U.S. PATENT DOCUMENTS

| | | | |
|---|---|---|---|
| 5,691,310 | A | 11/1997 | Vesely |
| 7,943,296 | B2 | 5/2011 | Silberbach et al. |
| 7,977,072 | B2 | 7/2011 | Bergmann et al. |
| 8,148,114 | B2 | 4/2012 | Mohapatra |
| 8,283,123 | B2 | 10/2012 | Vuolteenaho et al. |
| 2004/0063630 | A1 | 4/2004 | Schreiner |
| 2004/0176914 | A1 | 9/2004 | Buechler et al. |
| 2006/0019890 | A1 | 1/2006 | Kapoun et al. |
| 2006/0025367 | A1 | 2/2006 | Simari |
| 2006/0205642 | A1 | 9/2006 | Vesely |
| 2010/0285493 | A1 | 11/2010 | Bergmann et al. |
| 2012/0220528 | A1 | 8/2012 | Van Antwerp et al. |
| 2012/0277155 | A1 | 11/2012 | VanAntwerp et al. |

FOREIGN PATENT DOCUMENTS

| | | |
|---|---|---|
| CN | 103159847 A | 6/2013 |
| WO | 2006026663 A1 | 3/2006 |
| WO | 2007022123 A2 | 2/2007 |
| WO | 2007047504 A2 | 4/2007 |
| WO | 2013033675 A1 | 3/2013 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Joseph et al (Tex Heart Inst J 2009;36(6):510-20).*
Saito, Y., et al., "Clinical application of arial natriuretic polypeptide in patients with congestive heart failure: beneficial effects on left ventricular function", Circulation, American Heart Association, Dallas, Texas, Jul. 1987, vol. 76, No. 1, p. 115-124 (11 pages).
Vesely, D.L., et al., "Vessel Dilator Enhances Sodium and Water Excretion and Has Beneficial Hemodynamic Effects in Persons With Congestive Heart Failure", Circulation, American Heart Association, Dallas, Texas, Jul. 1998, vol. 98, No. 4, pp. 323-329 (8 pages).
Herrmann, H.C., et al., "Effects of atrial natriuretic factor on coronary hemodynamics and myocardial energetics in patients with heart failure", American Heart Journal, Jun. 1988, vol. 115, No. 6, pp. 1232-1238 (7 pages).
Elsner, D., et al., "Efficacy of prolonged infusion of urodilatin [ANP-(95-126)] in patients with congestive heart failure", American Heart Hournal, Apr. 1995, vol. 129, No. 4, pp. 766-773 (8 pages).
Serizawa, T., et al., "Acute hemodynamic Effects of alpha Human Atrial Natriuretic Polypeptide in Patients with Congestive Heart Failure", Japanese Heart Journal, Mar. 1988, vol. 29, No. 2, pp. 143-149 (7 pages).
Written Opinion of the International Searching Authority from International Application No. PCT/AU2011/001026, dated Dec. 5, 2011 (5 pages).
Vesely, D.L., et al., "Vessel Dilator, Long Acting Natriuretic Peptide, and Kaliuretic Peptide Increase Circulating Prostaglandin E2", Life Sciences, Elsevier Science Inc., USA, 2000, vol. 66, No. 10, pp. 905-913 (9 pages).
Vesely, D.L., et al., "Long-Acting Natriuretic Peptide, Vessel Dilator, and Kaliuretic Peptide Enhance the Urinary Excretion Rate of B2-Microglobulin", Metabolism, Dec. 2000, vol. 49, No. 12; pp. 1592-1597 (6 pages).

(Continued)

*Primary Examiner* — Brian J Gangle
*Assistant Examiner* — Andrea McCollum
(74) *Attorney, Agent, or Firm* — Hovey Williams LLP

(57) ABSTRACT

The present invention relates to a method of treating congestive heart failure (CHF) in a subject comprising administering a peptide derived from atrial natriuretic peptide (ANP) pro-hormone (eg vessel dilator; VSDL) or a mimetic thereof. In a particular application, the invention provides a method of treating the particular indication known as acute decompensated congestive heart failure (ADCHF). Devices for intravenous or subcutaneous infusion for use in the method of the invention are also disclosed.

6 Claims, 7 Drawing Sheets

(56) References Cited

OTHER PUBLICATIONS

Figure 2A:
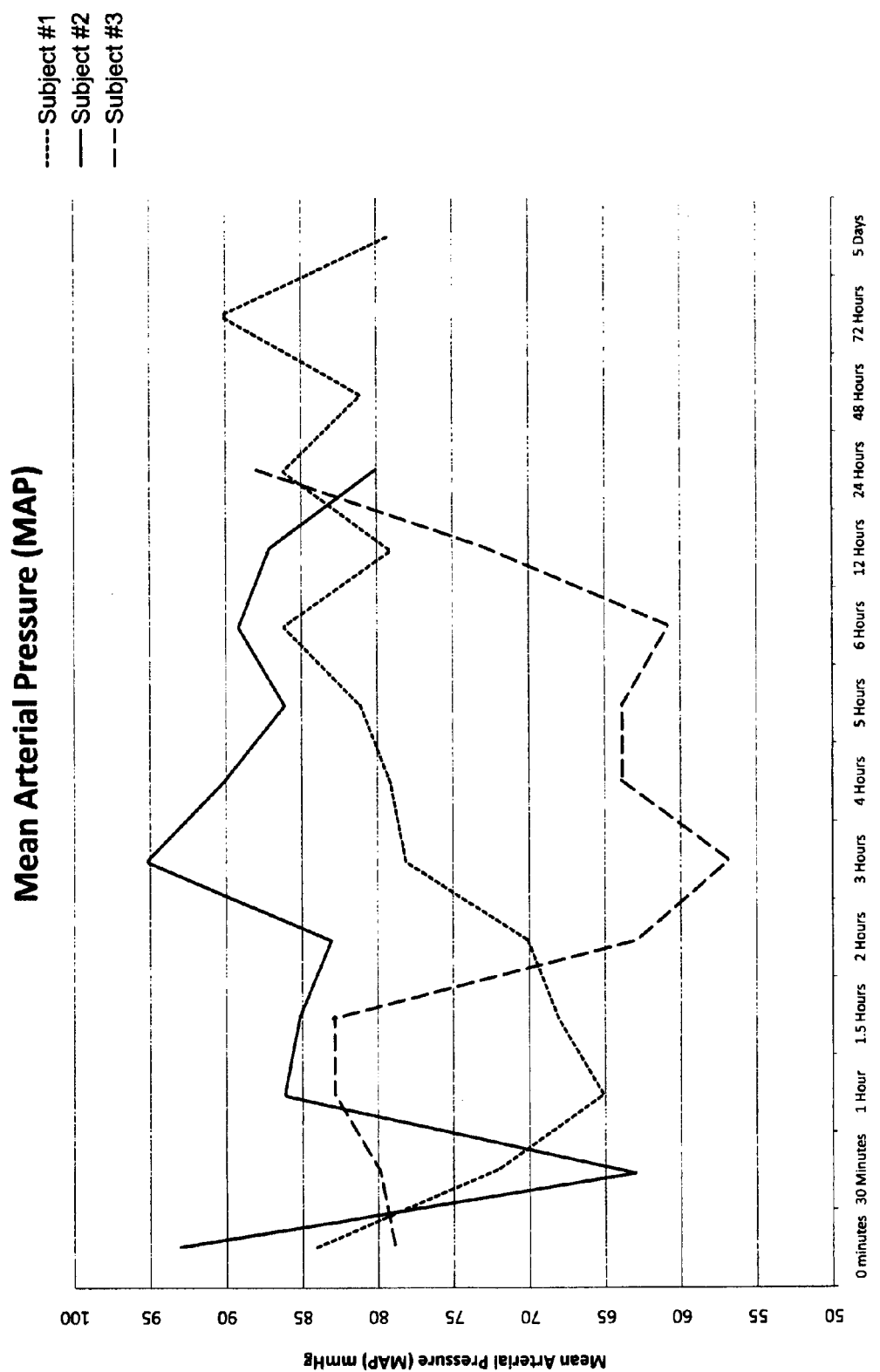
Figure 2B:
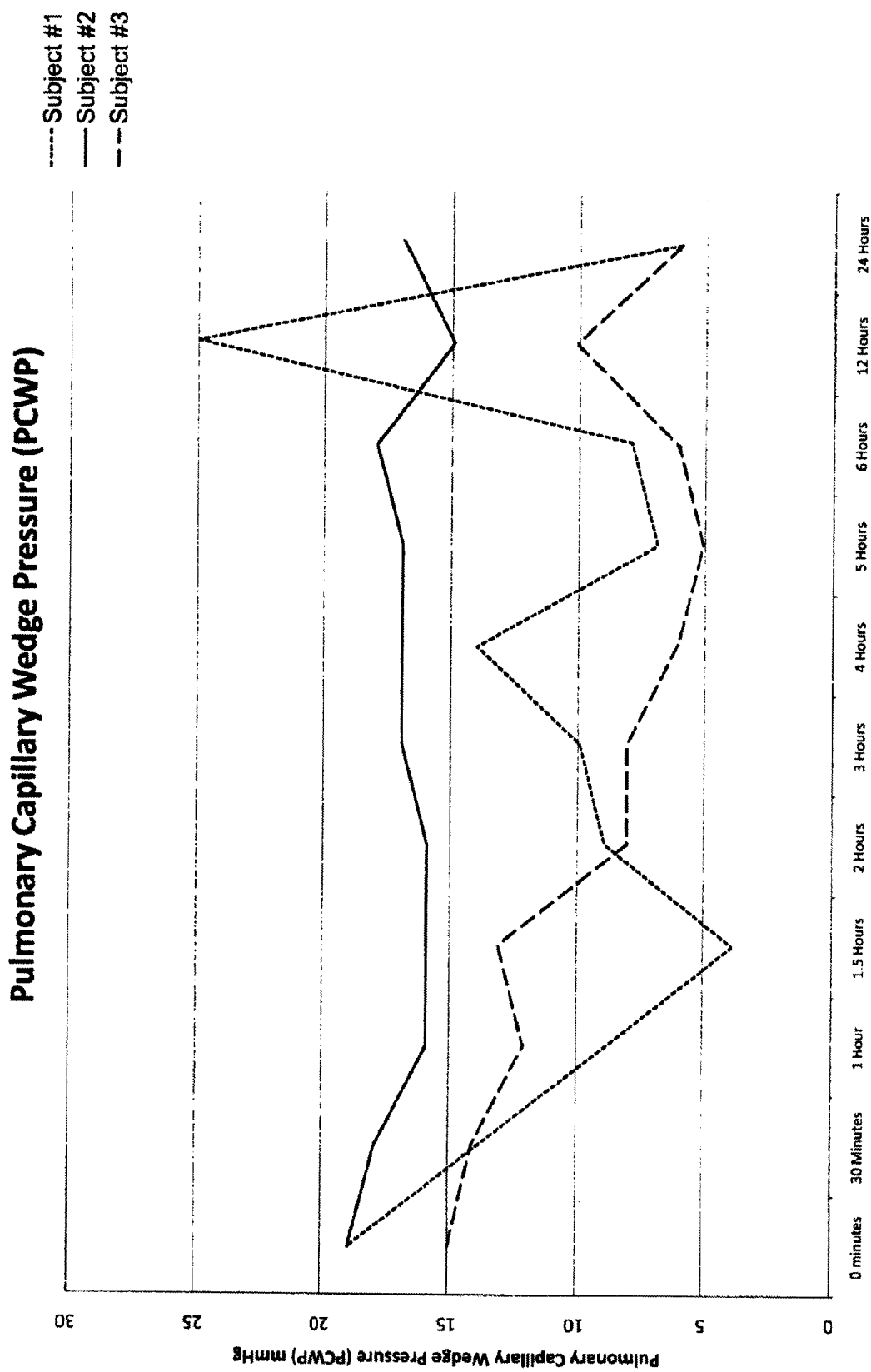
Figure 2C:
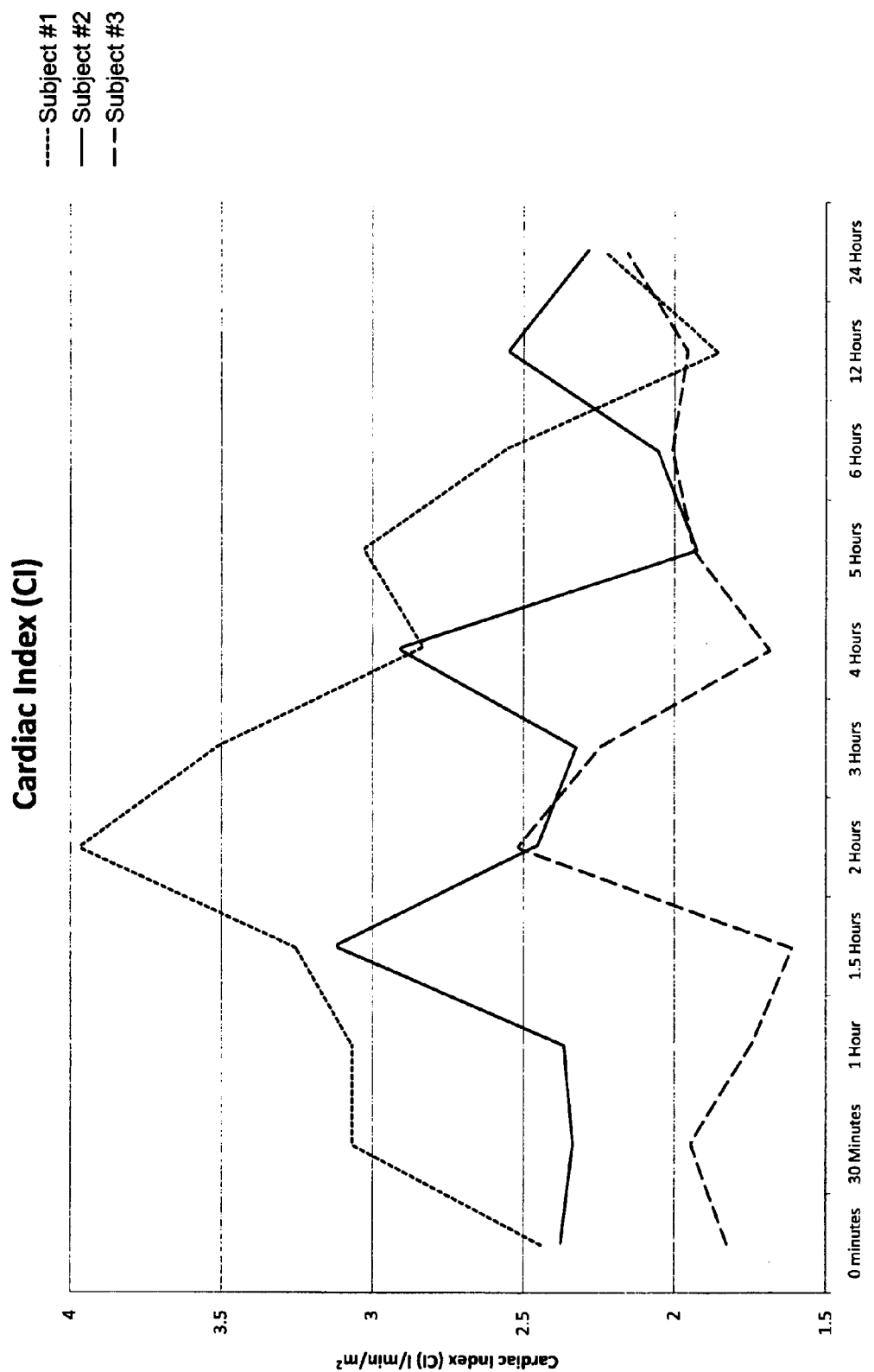
Figure 2D:
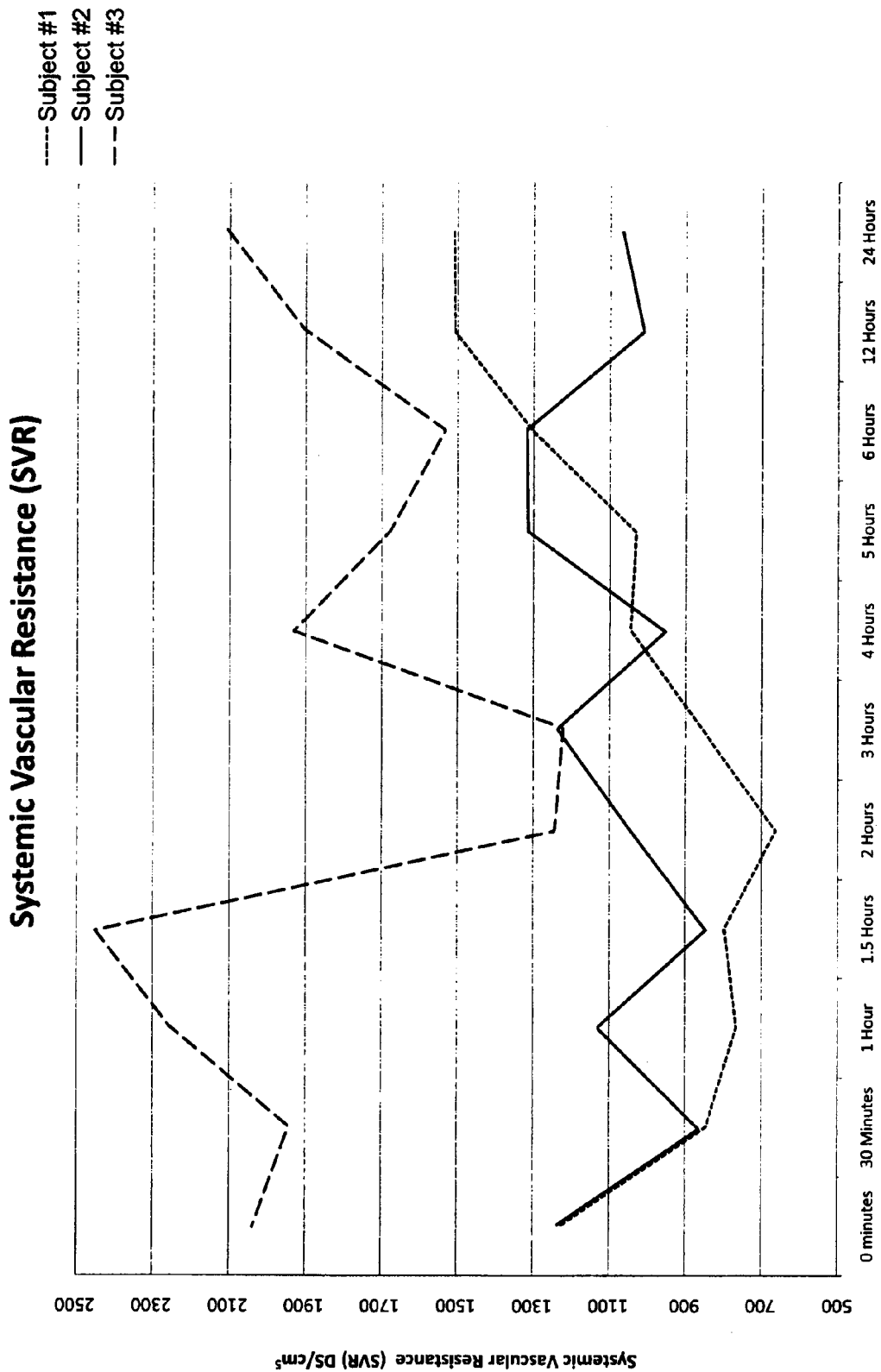
Figure 2E:
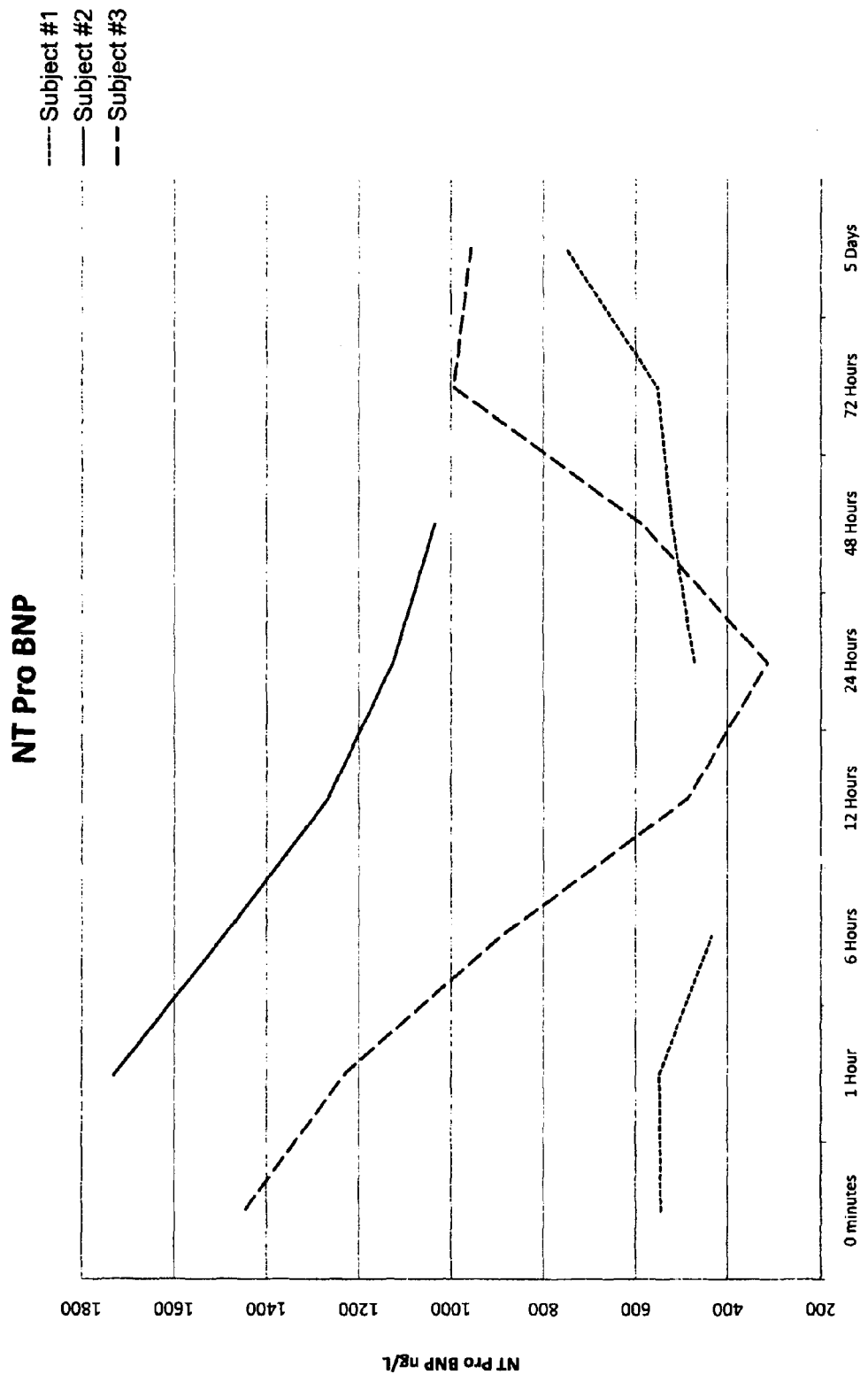

Vesely, D.L., et al., "Atrial Natriuretic Peptide Prohormone Gene Expression: Hormones and Diseases That Upregulate its Expression", IUBMB Life, 2002, 53: 153-159 (7 pages).

Vesely, D.L., et al., "Intact Negative Feedback of Four Cardiac Hormones in Congestive Heart Failure", Metabolism, May 2002, vol. 51, No. 5, pp. 582-588 (7 pages).

Patel, H., et al., "Combined Treatment with Vessel Dilator and Kaliuretic Hormone in Persons with Congestive Heart Failure", Experimental Biology and Medicine, 2004 229: pp. 521-527 (8 pages).

Vesely, D.L, et al., "Which of the Cardiac Natriuretic Peptides is Most Effective for the Treatment of Congestive Heart Failure, Renal Failure and Cancer?", Clinical and Experimental Pharmacology and Physiology, 2006, 33, pp. 169-176 (8 pages).

Vesely, D.L., et al., "Long-Acting Natriuretic Peptide, Vessel Dilator, and Kaliuretic Peptide Enhance Urinary Excretion Rate of Albumin, Total Protein, and $\beta 2$-Microglobulin in Patients With Congestive Heart Failure", Journal of Cardiac Failure, vol. 7, No. 1, Mar. 2001, pp. 55-63 (9 pages).

Vesely, D.L., et al., "Comparison of Vessel Dilator and Long-Acting Natriuretic Peptide in the Treatment of Congestive Heart Failure", American Heart Journal, Mosby, vol. 138, No. 4, Oct. 1999, pp. 625-632 (8 pages).

Vesely, D.L., et al., "Atrial Natriuretic Peptides in Pathophysiological Diseases", Cardiovascular Research, Oxford University Press, GB, vol. 51, 2001, pp. 647-658 (13 pages).

Vesely, D.L, "Discovery of New Cardiovascular Hormones for the Treatment of Congestive Heart Failure", Cardiovascular & Haematological Disorders—Drug Targets, vol. 7, Issue 1, Mar. 2007, pp. 47-62 (16 pages).

Supplementary European Search Report in corresponding EP 11 81 5913 dated Jun. 10, 2014 (3 pages).

\* cited by examiner

Figure 1

12.5 ng/kg/min for 60 minutes

| | | 0 minutes | 30 Minutes | 1 Hour | 1.5 Hours | 2 Hours | 3 Hours | 4 Hours | 5 Hours | 6 Hours | 12 Hours | 24 Hours | 48 Hours | 72 Hours | 5 Days |
|---|---|---|---|---|---|---|---|---|---|---|---|---|---|---|---|
| Subject #1 | Heart Rate | 84 | 78 | 82 | 84 | 84 | 83 | 83 | 83 | 87 | 87 | 90 | 82 | 80 | 75 |
| | Systolic BP | 104 | 97 | 90 | 93 | 97 | 111 | 108 | 110 | 111 | 102 | 109 | 102 | 115 | 98 |
| | Diastolic BP | 74 | 60 | 53 | 56 | 56 | 62 | 64 | 66 | 73 | 68 | 80 | 60 | 65 | 60 |
| | Mean Arterial BP | 84 | 72 | 65 | 68 | 70 | 78 | 79 | 81 | 86 | 79 | 86 | 81 | 90 | 79 |
| | PCWP | 19 | 14 | 9 | 4 | 9 | 10 | 14 | 7 | 8 | 25 | 6 | | | |
| | SVR | 1221 | 840 | 760 | 791 | 659 | 848 | 1039 | 1027 | 1295 | 1502 | 1504 | | | |
| | CI | 2.44 | 3.06 | 3.06 | 3.25 | 3.96 | 3.51 | 2.83 | 3.02 | 2.55 | 1.85 | 2.22 | | | |
| | NT ProBNP | 541 | | 544 | | | | | | 431 | | 469 | 517 | 548 | 746 |
| Subject #2 | Heart Rate | 97 | 88 | 92 | 90 | 90 | 97 | 95 | 96 | 97 | 89 | 89 | | | |
| | Systolic BP | 119 | 91 | 110 | 119 | 110 | 114 | 115 | 109 | 110 | 106 | 109 | | | |
| | Diastolic BP | 85 | 57 | 79 | 74 | 74 | 85 | 78 | 75 | 78 | 77 | 72 | | | |
| | Mean Arterial BP | 93 | 63 | 86 | 85 | 83 | 95 | 90 | 86 | 89 | 87 | 80 | | | |
| | PCWP | 19 | 18 | 16 | 16 | 16 | 17 | 17 | 17 | 18 | 15 | 17 | | | |
| | SVR | 1232 | 861 | 1124 | 843 | 1041 | 1230 | 951 | 1309 | 1313 | 1005 | 1061 | | | |
| | CI | 2.37 | 2.33 | 2.36 | 3.11 | 2.45 | 2.32 | 2.9 | 1.92 | 2.05 | 2.54 | 2.28 | | | |
| | NT ProBNP | | | 1735 | | | | | | 1500 | 1273 | 1131 | 1040 | | |
| Subject #3 | Heart Rate | 86 | 95 | 84 | 88 | 87 | 89 | 84 | 80 | 78 | 80 | 84 | 62 | 84 | 80 |
| | Systolic BP | 114 | 125 | 122 | 106 | 98 | 99 | 85 | 93 | 88 | 93 | 135 | 104 | 120 | 110 |
| | Diastolic BP | 62 | 58 | 64 | 72 | 46 | 36 | 53 | 49 | 48 | 63 | 65 | 59 | 65 | 60 |
| | Mean Arterial BP | 79 | 80 | 83 | 83 | 63 | 57 | 64 | 64 | 61 | 73 | 88 | | | |
| | PCWP | 15 | 14 | 12 | 13 | 8 | 8 | 6 | 5 | 6 | 10 | 6 | | | |
| | SVR | 2043 | 1950 | 2262 | 2453 | 1250 | 1228 | 1935 | 1683 | 1540 | 1909 | 2112 | | | |
| | CI | 1.82 | 1.94 | 1.74 | 1.61 | 2.51 | 2.24 | 1.68 | 1.93 | 2 | 1.95 | 2.15 | | | |
| | NT ProBNP | 1442 | | 1225 | | | | | | 886 | 481 | 311 | 580 | 989 | 953 |

*Figure 1*

SEQUENCE LISTING

```
<160> NUMBER OF SEQ ID NOS: 4

<210> SEQ ID NO 1
<211> LENGTH: 37
<212> TYPE: PRT
<213> ORGANISM: Homo sapiens

<400> SEQUENCE: 1

Glu Val Val Pro Pro Gln Val Leu Ser Glu Pro Asn Glu Glu Ala Gly
1               5                   10                  15

Ala Ala Leu Ser Pro Leu Pro Glu Val Pro Pro Trp Thr Gly Glu Val
            20                  25                  30

Ser Pro Ala Gln Arg
        35

<210> SEQ ID NO 2
<211> LENGTH: 37
<212> TYPE: PRT
```

```
<213> ORGANISM: Pongo pygmaeus

<400> SEQUENCE: 2

Glu Val Val Pro Pro Gln Val Leu Ser Glu Gln Asn Glu Glu Ala Gly
1               5                   10                  15

Ala Ala Leu Ser Pro Leu Pro Glu Val Pro Pro Trp Thr Gly Glu Val
            20                  25                  30

Ser Pro Ala Gln Arg
        35

<210> SEQ ID NO 3
<211> LENGTH: 37
<212> TYPE: PRT
<213> ORGANISM: Macaca mulatta

<400> SEQUENCE: 3

Glu Val Val Pro Pro Gln Val Leu Arg Glu Gln Asn Glu Glu Ala Gly
1               5                   10                  15

Ala Ala Leu Ser Pro Leu Pro Glu Val Pro Pro Trp Thr Gly Asp Val
            20                  25                  30

Ser Pro Ala Gln Arg
        35

<210> SEQ ID NO 4
<211> LENGTH: 37
<212> TYPE: PRT
<213> ORGANISM: Felis catus

<400> SEQUENCE: 4

Glu Val Val Pro Pro Gln Val Leu Ser Glu Gln Asn Glu Glu Ala Gly
1               5                   10                  15

Ala Ala Leu Ser Pro Leu Pro Glu Val Pro Pro Trp Ala Gly Glu Val
            20                  25                  30

Asn Pro Ala Gln Arg
        35
```

THERAPEUTIC METHOD FOR TREATING CONGESTIVE HEART FAILURE

INCORPORATION BY REFERENCE

This patent application is the National Stage of International Patent Application No. PCT/AU2011/001026, filed Aug. 11, 2011, which claims priority from:
U.S. Provisional Patent Application No. 61/445,814 titled "Therapeutic method 2" filed 23 Feb. 2011; and
U.S. Provisional Patent Application No. 61/445,826 titled "Therapeutic method 3" filed 23 Feb. 2011.
The entire content of these applications is hereby incorporated by reference.
In addition, the following patent is referred to herein:
U.S. Pat. No. 5,691,310 titled "Methods of treatment using proANF peptides".
The entire content of this patent is hereby incorporated by reference.

SEQUENCE LISTING

The suquences listed in the accompanying Sequence Listing are presented in accordance with 37 C.F.R. 1.822. The Suquence Listing is submitted as an ASCII computer readable text file, which is incorporated by reference herein.

FIELD OF THE INVENTION

The present invention relates to a method of treating congestive heart failure (CHF) in a subject. In a particular application, the invention provides a method of treating the particular indication known as acute decompensated congestive heart failure (ADCHF).

BACKGROUND TO THE INVENTION

CHF is a major health problem affecting over 23 million people worldwide causing significant morbidity and mortality[1]. CHF occurs when the heart inadequately pumps oxygenated blood to the rest of the body, resulting in the retention of fluid (oedema), shortness of breath (dyspnea) and lethargy. Often, it is also accompanied by renal failure as the kidneys strain to maintain glomerular filtration in an attempt to excrete the build up of excess fluids[2]. CHF may be caused by one or a combination of factors including: weakened heart muscle, damaged heart valves, blocked blood vessels supplying the heart muscle (ie cardiac arteries), high blood pressure leading to a thickening of the heart muscle (ie left ventricular hypertrophy), congenital heart disease, prolonged arrhythmias, infections, and life style factors such as smoking, obesity and alcohol or drug (eg cocaine) consumption which can, for example, be the cause of long term, uncontrolled high blood pressure (hypertension) that may damage the heart muscle and blood vessels. If steps are not taken to treat CHF when it becomes apparent and/or modify patient life style, the CHF may become a long term (ie chronic) condition. The severity of symptoms of patients with chronic CHF can progress to a level where there is a "marked limitation in activity [and the patient is] comfortable only at rest" as per Class III of the New York Heart Association (NYHA) CHF functional classification. Consequently, patients with chronic CHF that has progressed to NYHA class III can require frequent hospitalisation and/or palliative care. Moreover, while such chronic CHF is generally stable, it may easily decompensate to the often critical state known as acute decompensated congestive heart failure (ADCHF). This can be caused for a variety of reasons including arrhythmias, ischaemia, illness such as pneumonia and poor compliance with diet and medications[19].

In the United States alone, over 1.1 million people are admitted to hospital every year with ADCHF[1], 10% of which die in care and 40% of which die within the year. Further, it has been reported that over 6.5 million days of hospitalisation per year in the United States are attributable to ADCHF[3]. These costs account for almost 50% of the US$34 billion spent each year on heart failure care in the United States. Unfortunately, ADCHF remains as an unmet clinical need, with current monotherapeutic and polytherapeutic treatments being effectively, and efficaciously, limited at alleviating symptoms only.

Vessel dilator (VSDL) is a naturally occurring 37 amino acid (aa) cardiac peptide consisting of amino acids 31-67 of the 126 aa atrial natriuretic peptide (ANP) prohormone[4, 6 and 7]. Like other natriuretic peptides, the main biological activity of VSDL is to regulate blood pressure and maintain plasma volume in healthy individuals by mediating natriuretic, diuretic and haemodynamic effects[4]. Preliminary studies on VSDL's effect in CHF have been conducted via both preclinical and human clinical studies[8, 9]. One of the first studies exploring the use of synthetic VSDL in a CHF animal model was in normal and compensated aorto-caval (AV) fistula dogs, resulting in similar significant reductions in arterial blood pressure, right atrial pressure and elevations in urinary sodium excretion[5]. The human studies have involved patients with chronic, but stable, New York Heart Association (NYHA) Class III CHF[10], and have shown that VSDL can significantly improve natriuretic, diuretic and haemodynamic parameters without any symptomatic side effects. In particular, it has been shown that VSDL is able to increase urine flow 2- to 13-fold, and urine flow was still increased ($P<0.001$) 3 hours after the VSDL infusion was halted[10]. Further, it was found that VSDL enhanced sodium excretion 3- to 4-fold in CHF patients ($P<0.01$), and was still significantly ($P<0.01$) elevated 3 hours after infusion. Moreover, it was found that VSDL could: decrease systemic vascular resistance (SVR) (24%); decrease pulmonary vascular resistance (PVR) (25%); decrease pulmonary capillary wedge pressure (PCWP) (33%); decrease central venous pressure (CVP) (27%); increase cardiac output (CO) (34%); increase cardiac index (CI) (35%); and increase stroke volume index (SVI) (24%); without significantly affecting heart rate or pulmonary artery pressure in the CHF patients. In addition, it is also known that VSDL promotes the synthesis of the renal protective agent, prostaglandin $E_2$ ($PGE_2$), and can increase circulating $PGE_2$ 8-fold compared to basal levels[11]. $PGE_2$ also benefits CHF patients by decreasing mean arterial pressure and total peripheral resistance while increasing stroke volume index and cardiac output.

It has been reported that VSDL circulates in healthy humans at significantly higher basal levels than other atrial natriuretic peptides, including ANP and B-type natriuretic peptide (BNP), where the circulating concentration of VSDL is 17-fold and 48-fold higher than ANP and BNP respectively. Hitherto the studies described herein, this was believed to owe, in part, to VSDL possessing a significantly longer circulatory $t_{1/2}$ of ~120 minutes and biological $t_{1/2}$ of ~>6 hours. In comparison, it has been reported that BNP has a circulating $t_{1/2}$ of ~3.1 minutes and biological $t_{1/2}$ of ~<½ hour[4, 6-9, 12 and 13]. In patients with volume overload, including those with CHF, circulating natriuretic peptides are elevated. This is thought to be indicative of a compensatory mechanism attempting to reinstate homeostasis. However, in severe congestion, it appears that the body is unable to produce sufficient quantities to restore balance.

The present applicant has now recognised that the benefits demonstrated in preclinical and clinical use of VDSL in the treatment of CHF are superior to those seen with the current natriuretic treatments for ADCHF[14], and hereby proposes VSDL administration to patients with chronic CHF or ADCHF as a safe and effective treatment for mediating beneficial haemodynamic effects with additional beneficial natriuretic, diuretic and renal effects, whilst regulating plasma volume and blood pressure (BP) within clinically acceptable ranges and without seriously adverse side effects. It is also anticipated that such VSDL treatment may reduce hospitalisation time and readmission rates for chronic CHF and ADCHF patients. Further, the present applicant has found that effective treatment of chronic CHF and ADCHF patients with VSDL can be achieved with doses that are substantially lower than expected.

SUMMARY OF THE INVENTION

In its broadest aspect, the present invention provides a method of treating chronic congestive heart failure (CHF) or acute decompensated congestive heart failure (ADCHF) in a subject, said method comprising administering to the subject an effective amount of a peptide derived from atrial natriuretic peptide (ANP) prohormone or a mimetic thereof.

Preferably, the method is used for treating chronic CHF with a symptom severity level of NYHA class III or, more preferably, ADCHF with a symptom severity level of NYHA class III or IV (ie where the subject shows "severe limitations [and] experiences symptoms even while at rest").

The method may be suitable for the treatment of non-human primates and other mammals such as livestock (including race horses), exotic animals (eg tigers and elephants) and companion animals (eg dogs and cats), however typically the subject will be a human, in which case, the method is most preferably used for treating ADCHF characterised by:
1. Dyspnoea at rest or dyspnoea with minimal activity (ie difficulty breathing at rest while sitting, or difficulty breathing while lying flat or with one pillow, or difficulty breathing with minimal activity such as talking, eating); and
2. At least one of the following signs:
   Tachypnoea with respiratory rate >20 breaths per minute, or
   Pulmonary congestion/oedema with rales or crackles/crepitations at least a third above lung bases; and
3. At least one of the following objective measures:
   Pulmonary oedema/congestions as shown by chest X-ray, or
   Circulating B-type natriuretic peptide (BNP) concentration of ≥400 pg/ml or circulating NT-proBNP concentration of ≥1000 pg/ml, or
   A PCWP >20 mmHg or
   A systolic dysfunction within the last 12 months (EF<50%) as determined by Trans-Thoracic Echocardiogram (TTE), nuclear testing, cardiac magnetic resonance imaging (MRI) or ventricular angiography).

The term "effective amount" as used herein refers to an amount of the peptide or mimetic that will elicit a desired biological or therapeutic response in the subject (eg beneficial haemodynamic effects with, preferably, additional beneficial natriuretic, diuretic and renal effects whilst regulating plasma volume and blood pressure (BP) within clinically acceptable ranges). The effective amount will, however, typically be in the range of 0.1 to 75 µg/kg/day. The effective amount of the peptide or mimetic is administered by infusion (preferably, by intravenous (iv) or subcutaneous (sc) infusion) as a single dose per day or, otherwise, across multiple times per day (eg 2 to 4 times per day). The effective amount of the peptide or mimetic may, for example, be administered by infusion at a rate of <100 ng/kg/min, and preferably, at a rate of about ≤75 ng/kg/min, more preferably at a rate of about ≤50 ng/kg/min or ≤30 ng/kg/min, still more preferably at a rate of about ≤25 ng/kg/min, even still more preferably ≤20 ng/kg/min and, and yet still more preferably, at a rate of about ≤15 ng/kg/min.

In a further aspect, the present invention provides the use of a peptide derived from atrial natriuretic peptide (ANP) prohormone or a mimetic thereof in the manufacture of a medicament for infusion of the peptide or mimetic, for treating chronic congestive heart failure (CHF) or acute decompensated congestive heart failure (ADCHF) in a subject.

In a still further aspect, the present invention provides an infusion device containing, or provided with, a medicament comprising a peptide derived from atrial natriuretic peptide (ANP) prohormone or a mimetic thereof adapted for infusion of the peptide or mimetic, for treating chronic congestive heart failure (CHF) or acute decompensated congestive heart failure (ADCHF) in a subject.

BRIEF DESCRIPTION OF THE ACCOMPANYING FIGURES

Figure 3:
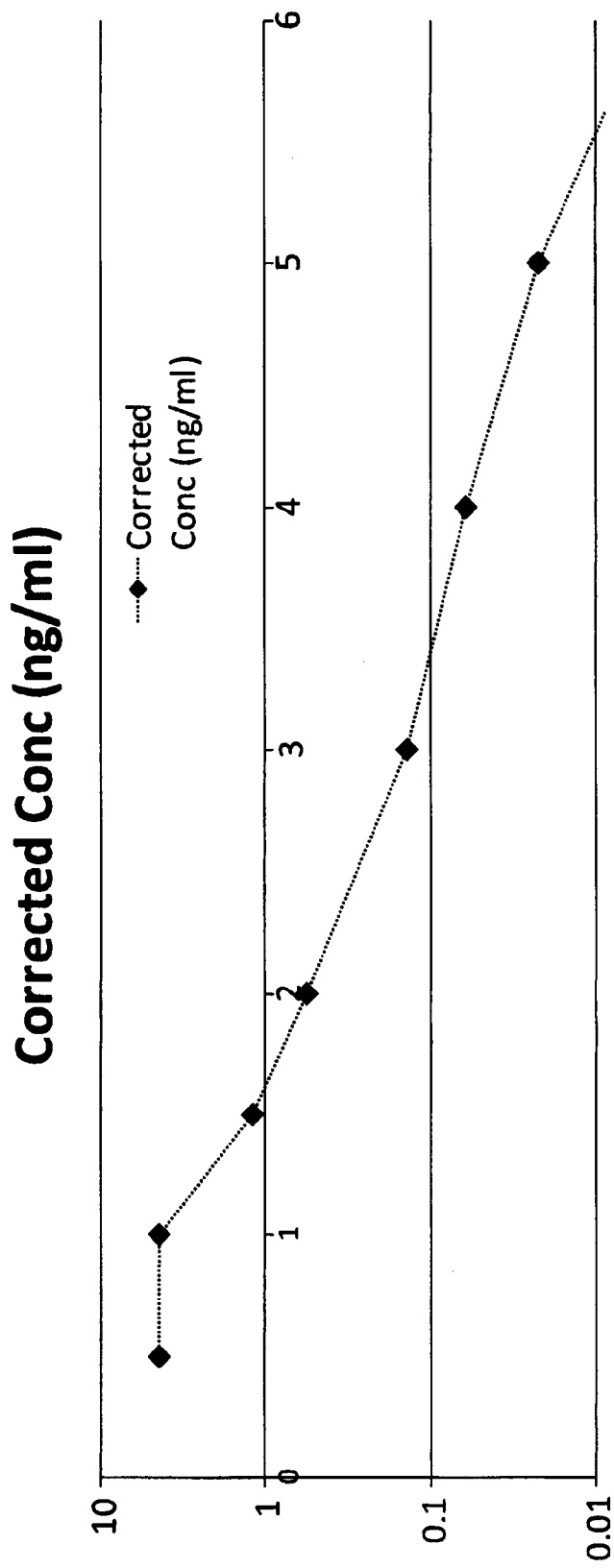

FIG. 1 provides tabulated response data for three ADCHF patients infused intravenously (iv) with 12.5 ng/kg/min for 60 minutes recorded from commencement of infusion (0 minutes) to 5 days post-infusion as indicated;

FIG. 2 provides graphical representations of the results of FIG. 1: (A) Mean arterial pressure (MAP), (B) Pulmonary capillary wedge pressure (PCWP), (C) Cardiac index (CI), (D) Systemic vascular resistance (SVR), and (E) NT-proBNP circulatory levels (ng/L); and FIG. 3 provides a graphical representation of measured VSDL concentrations in blood samples taken at the various time points, as corrected for a baseline (ie endogenous) VSDL concentration of 0.024 ng/ml.

DETAILED DESCRIPTION OF THE INVENTION

The present invention relates to the use of a peptide derived from atrial natriuretic peptide (ANP) prohormone (eg VSDL) or a mimetic thereof, in a method for the treatment of chronic CHF or ADCHF in a subject comprising administering to a subject an effective amount of the peptide or mimetic (typically in the range of 0.1 to 75 µg/kg/day).

In a first embodiment, the present invention provides a method of treating chronic congestive heart failure (CHF) or acute decompensated congestive heart failure (ADCHF) in a subject, said method comprising administering to the subject an effective amount of a peptide derived from atrial natriuretic peptide (ANP) prohormone or a mimetic thereof by infusion at a rate of 1 to 400 ng per kg subject body weight per minute (ng/kg/min).

In this embodiment, the effective amount of the peptide or mimetic will preferably be in the range of 0.1 to 75 µg/kg/day, but more preferably in the range of about 0.1 to 25 µg/kg/day, still more preferably in the range of about 0.1 to 20 µg/kg/day or about 0.1 to 5 µg/kg/day, and even still more preferably, in the range of about 0.1 to 3.5 µg/kg/day or 0.1 to 1.5 µg/kg/day. Most preferably, the effective amount that is administered to the subject will be about 0.75 µg/kg/day.

The effective amount of the peptide or mimetic may, for example, be administered by infusion at a rate of <100 ng/kg/min, and preferably, at a rate of about ≤75 ng/kg/min, more preferably at a rate of about ≤50 ng/kg/min or ≤30 ng/kg/min, still more preferably at a rate of about ≤25 ng/kg/min, even still more preferably ≤20 ng/kg/min and, and yet still more preferably, at a rate of about ≤15 ng/kg/min. Most preferably, the effective amount is infused at a rate in the range of 1 to 15 ng/kg/min and, in one particularly preferred form of the method of the first embodiment, the effective amount of the peptide or mimetic is administered to the subject by infusion at a rate of about 12.5 ng/kg/min.

The effective amount of the peptide or mimetic may be infused (preferably, by intravenous (iv) or subcutaneous (sc) infusion) as a single dose per day or, otherwise, across multiple times per day (eg as three equal separate doses at 0 hours, 6 hours and 12 hours).

Typically, a single dose (or each dose of a multidose regimen), will be infused over a period of about 60 minutes.

Where the rate of the infusion is at a preferred rate of ≤75 ng/kg/min, it is considered that a single dose over a period of about 60 minutes will provide an effective daily dose (ie of ≤4.5 µg/kg/day). Further, where lower infusion rates are employed of 25 ng/kg/min and 12.5 ng/kg/min, it is considered that a single dose over a period of 60 minutes will provide an effective daily dose of ≤51.5 µg/kg/day and ≤0.75 µg/kg/day, respectively.

Thus, in a second embodiment, the present invention provides a method of treating chronic congestive heart failure (CHF) or acute decompensated congestive heart failure (ADCHF) in a subject, said method comprising administering to the subject an effective amount of a peptide derived from atrial natriuretic peptide (ANP) prohormone or a mimetic, wherein said effective amount is ≤4.5 µg/kg/day.

In this embodiment, the effective amount of the peptide or mimetic will preferably be in the range of 0.1 to 3.5 µg/kg/day, but more preferably in the range of about 0.1 to 1.5 µg/kg/day. Most preferably, the effective amount that is administered to the subject will be about 0.75 µg/kg/day.

Preferably, the method of the present invention is used for treating chronic CHF with a symptom severity level of NYHA class III or, more preferably, ADCHF with a symptom severity level of NYHA class III or IV. Most preferably, the method is used for treating ADCHF in a human characterised by:
1. Dyspnoea at rest or dyspnoea with minimal activity (ie difficulty breathing at rest while sitting, or difficulty breathing while lying flat or with one pillow, or difficulty breathing with minimal activity such as talking, eating); and
2. At least one of the following signs:
   Tachypnoea with respiratory rate >20 breaths per minute, or
   Pulmonary congestion/oedema with rales or crackles/crepitations at least a third above lung bases; and
3. At least one of the following objective measures:
   Pulmonary oedema/congestions as shown by chest X-ray, or
   Circulating B-type natriuretic peptide (BNP) concentration of ≥400 pg/ml or circulating NT-proBNP concentration of ≥1000 pg/ml, or
   A PCWP >20 mmHg or
   A systolic dysfunction within the last 12 months (EF<50%) as determined by Trans-Thoracic Echocardiogram (TTE), nuclear testing, cardiac magnetic resonance imaging (MRI) or ventricular angiography).

The method utilises a peptide derived from ANP prohormone or a mimetic thereof.

It is to be understood that suitable peptides derived from ANP prohormone include the proANP 1-30, proANP 31-67 and proANP 79-98 peptides of human ANP prohormone described in U.S. Pat. No. 5,691,310, as well as derivatives of said peptides such as derivatives which include minor variations in the amino acid sequence which do not result in any substantial decrease or variation in biological activity. These variations may include conservative amino acid substitutions such as: Gly, Ala, Val, Ile, Leu, Met; Asp, Glu, Asn, Gln; Ser, Thr; Lys, Arg, His; Phe, Tyr, Trp, His; and Pro, Nα-alkylamino acids; and non-conservative amino acid substitutions. Some specific examples of suitable amino acid substitutions within the ANP prohormone sequence include: Ser→Arg (especially at position 39), Pro→Gln (especially at position 41), Thr→Ala (especially at position 59), Glu→Asp (especially at position 61), and Ser→Asn (especially at position 63).

Suitable mimetics of a peptide derived from ANP prohormone may be designed using any of the methods well known to the person skilled in the art for designing mimetics of peptides based upon amino acid sequences in the absence of secondary and tertiary structural information[15]. For example, peptide mimetic compounds may be produced by modifying amino acid side chains to increase the hydrophobicity of defined regions of the peptide (eg substituting hydrogens with methyl groups on aromatic residues of the peptides), substituting amino acid side chains with non-amino acid side chains (eg substituting aromatic residues of the peptides with other aryl groups), and substituting amino- and/or carboxy-termini with various substituents (eg substituting aliphatic groups to increase hydrophobicity). Alternatively, mimetic compounds of a peptide derived from ANP prohormone may be a so-called peptoid (ie non-peptide) which includes modification of the peptide backbone (ie introducing amide bond surrogates by, for example, replacing the nitrogen atoms in the backbone with carbon atoms), or includes N-substituted glycine residues, one or more D-amino acids (in place of L-amino acid(s)) and/or one or more α-amino acids (in place of β-amino acids or γ-amino acids). Further, suitable mimetic compounds of a peptide derived from ANP prohormone include "retro-inverso peptides" where the peptide bonds are reversed and D-amino acids assembled in reverse order to the order of the L-amino acids in the peptide sequence upon which the mimetic is based, and other non-peptide frameworks such as steroids, saccharides, benzazepine 1,3,4-trisubstituted pyrrolidinone, pyridones and pyridopyrazines.

Preferably, the method of the present invention comprises the administration of proANP 31-67 (ie a peptide consisting of the amino acids 31-67 of the ANP prohormone), known as vessel dilator (VSDL), or a derivative thereof. The amino acid sequence of the preferred, human, VSDL is as follows:

(SEQ ID NO: 1)
Glu-Val-Val-Pro-Pro-Gln-Val-Leu-Ser-Glu-Pro-Asn-Glu-Glu-Ala-Gly-Ala-Ala-Leu-

Ser-Pro-Leu-Pro-Glu-Val-Pro-Pro-Trp-Thr-Gly-Glu-Val-Ser-Pro-Ala-Gln-Arg.

Other suitable VSDL peptides include:

*Pongo pygmaeus* (Common Orang-utan)

(SEQ ID NO: 2)
Glu-Val-Val-Pro-Pro-Gln-Val-Leu-Ser-Glu-Gln-Asn-Glu-Glu-Ala-Gly-Ala-Ala-Leu-

Ser-Pro-Leu-Pro-Glu-Val-Pro-Pro-Trp-Thr-Gly-Glu-Val-Ser-Pro-Ala-Gln-Arg;

*Macaca mulatta* (Rhesus Monkey)

(SEQ ID NO: 3)
Glu-Val-Val-Pro-Pro-Gln-Val-Leu-Arg-Glu-Gln-Asn-Glu-Glu-Ala-Gly-Ala-Ala-Leu-

Ser-Pro-Leu-Pro-Glu-Val-Pro-Pro-Trp-Thr-Gly-Asp-Val-Ser-Pro-Ala-Gln-Arg;

and

*Felis catus*

(SEQ ID NO: 4)
Glu-Val-Val-Pro-Pro-Gln-Val-Leu-Ser-Glu-Gln-Asn-Glu-Glu-Ala-Gly-Ala-Ala-Leu-

Ser-Pro-Leu-Pro-Glu-Val-Pro-Pro-Trp-Ala-Gly-Glu-Val-Asn-Pro-Ala-Gln-Arg.

Peptides derived from ANP prohormone may be produced by any of the standard protein synthesis methods well known to the person skilled in the art or, more preferably, by recombinant techniques involving, for example, the introduction of a polynucleotide molecule encoding the particular peptide into a suitable host cell (eg a host cell selected from bacterial cells such as *E. coli, Streptomyces* and *S. typhimurium*; fungal cells such as yeast cells; insect cells such as *Drosophila* S2 and *Spodoptera* Sf9 cells; animal cells such as Chinese hamster ovary (CHO), monkey kidney (COS) cells and human embryonic kidney 293 (HEK 293) cells; and plant cells) and culturing the cell under conditions suitable for the expression of the particular peptide.

Preferably, the peptide derived from ANP prohormone or a mimetic thereof will be administered as a composition consisting of a simple solution or suspension of the peptide or mimetic in a pharmaceutically-acceptable carrier. However, it will be readily appreciated by the person skilled in the art, that the peptide or mimetic may be bound or associated with a carrier molecule (eg a carrier protein or fusion partner such as human serum albumin (HSA) or a polysaccharide (eg Dextran) or polyether (eg polyethylene glycol)) in order to modulate the biological activity and/or serum half-life time of the peptide or mimetic.

The term "pharmaceutically-acceptable carrier" as used herein refers to any pharmaceutically- or veterinary-acceptable solvent, suspending agent or vehicle for delivering the peptide derived from ANP prohormone or mimetic thereof to the subject. The carrier may include one or more pharmaceutical additives of a type appropriate to, for example, iv administration (eg excipients, preservatives, stabilisers etc).

The peptide derived from ANP prohormone or a mimetic thereof may be administered to the subject in a combination therapy. However, while it is considered that the administration of such a peptide (eg VSDL) or mimetic thereof should not cause clinically significant hypotension, they can be vasodilatory and, therefore, it is preferred that any combination therapy avoids other vasodilatory agents which may cause a synergetic blood pressure lowering. For that reason, the method of the present invention may not be suitable for subjects already using vasodilatory agents.

The administration of the peptide derived from ANP prohormone or a mimetic thereof by infusion is, preferably, achieved intravenously (iv) (which is particularly suitable in the hospital setting) or subcutaneously (sc) (which is suitable for both hospitalised patient and out-of-hospital administration). For example, infusion may be via a standard catheter or implantable drug port (eg a Port-a-Cath®; Smiths Medical MD, Inc., St. Paul Minn., United States of America), or otherwise achieved using a drug infusion pump (eg implantable drug infusion pumps such as an Alzet® osmotic pump (Durect Corporation, Cupertino Calif., United States of America) and a Duros® device (Intarcia Therapeutics, Inc., Hayward Calif., United States of America), or a drug infusion pump for subcutaneous (sc) administration such as a Paradigm™ device (Medtronic Australasia Pty Ltd, Gladesville NSW, Australia) all of which can provide a controlled release of the peptide or mimetic) which preferably infuses the peptide or mimetic at a constant rate.

The use of an implantable drug port or drug infusion pump will be particularly well suited for a long term treatment method according to the present invention. Typically, the peptide or mimetic will be infused at a constant rate, however, in some cases it may be desirable to employ a drug infusion pump employing a feedback control mechanism (eg a feedback linked to measurement of oedema (in the lung) or other surrogate marker) to control release of the peptide or mimetic.

In one particularly preferred embodiment, the invention provides a method of treating ADCHF in a subject, said method comprising administering to the subject an effective amount of VSDL, wherein said effective amount is in the range of about 0.1 to 20 µg/kg/day and is administered by infusion, preferably intravenous (iv) or subcutaneous (sc) infusion, at a rate of ≤50 ng/kg/min.

In another particularly preferred embodiment, the invention provides a method of treating ADCHF in a subject, said method comprising administering to the subject an effective amount of VSDL, wherein said effective amount is in the range of about 0.1 to 1.5 µg/kg/day and is administered by infusion, preferably intravenous (iv) or subcutaneous (sc) infusion.

It will be appreciated by the person skilled in the art that numerous variations and/or routine modifications may be made to the method of the present invention without departing from the spirit or scope of the invention as broadly described. For example, it will be understood that the effective amount and frequency of administration of the peptide or mimetic for any particular subject may be varied and will depend upon a variety of factors including the activity of the particular peptide or mimetic that is utilised, the metabolic stability and length of action of the particular peptide or mimetic, the age, body weight, general health, sex and diet of the particular subject, and the time of administration, rate of excretion, drug combination and severity of the chronic CHF or ADCHF being treated.

The present invention further provides the use of a peptide derived from atrial natriuretic peptide (ANP) prohormone or a mimetic thereof in the manufacture of a medicament for infusion at a rate of about 1 to 400 ng per kg subject body weight per minute (ng/kg/min), for treating chronic congestive heart failure (CHF) or acute decompensated congestive heart failure (ADCHF) in a subject. In such use, preferably, the medicament is capable of providing an effective amount of the peptide or mimetic in the range of about in the range of 0.1 to 75 µg/kg/day, but more preferably in the range of about 0.1 to 25 µg/kg/day, still more preferably in the range of about 0.1 to 20 µg/kg/day or about 0.1 to 5 µg/kg/day, and even still more preferably, in the range of about 0.1 to 3.5 µg/kg/day or 0.1 to 1.5 µg/kg/day.

Alternatively, the present invention provides the use of a peptide derived from atrial natriuretic peptide (ANP) prohormone or a mimetic thereof in the manufacture of a medicament for treating chronic congestive heart failure (CHF) or acute decompensated congestive heart failure (ADCHF) in a subject, wherein said medicament is adapted to provide said subject with an effective amount of said peptide or mimetic of ≤4.5 µg/kg/day. In such use, preferably, the medicament is capable of providing an effective amount of the peptide derived from atrial natriuretic peptide (ANP) prohormone or a mimetic in the range of 0.1 to 3.5 µg/kg/day, but more preferably in the range of about 0.1 to 1.5 µg/kg/day.

Most preferably, in the use of the present invention, the medicament is capable of providing an effective amount of the peptide or mimetic of about 0.75 µg/kg/day.

The medicament may, for example, be adapted for infusion at a rate of <100 ng/kg/min, and preferably at a rate of about ≤75 ng/kg/min, more preferably at a rate of about ≤50 ng/kg/min or ≤30 ng/kg/min, still more preferably at a rate of about ≤25 ng/kg/min, even still more preferably ≤20 ng/kg/min and, and yet still more preferably at a rate of about ≤15 ng/kg/min. Most preferably, the medicament is adapted for infusion at a rate of about 12.5 ng/kg/min.

The medicament may be used in a single dose per day or administered across multiple times per day (eg 2 to 4 times per day). Typically, a single dose (or each dose of a multidose regimen) will be administered over a period of about 60 minutes.

Preferably, the medicament is intended for treating the particular indication of ADCHF with a symptom severity level of NYHA class III or IV.

Preferably, the use of the present invention is a use of VSDL or a derivative thereof.

The medicament may be infused intravenously (iv) via a standard catheter, implantable drug port or drug infusion pump, or subcutaneously (sc) via a drug infusion pump.

In one particularly preferred embodiment, the invention provides the use of VSDL in the manufacture of a medicament for infusion at a rate of ≤50 ng/kg/min, for treating ADCHF in a subject.

In another particularly preferred embodiment, the invention provides the use of VSDL in the manufacture of a medicament for treating ADCHF in a subject, wherein said medicament is adapted to provide said subject with an effective amount of said peptide or mimetic in the range of about 0.1 to 1.5 µg/kg/day.

The present invention still further provides an infusion device containing, or provided with, a medicament comprising a peptide derived from atrial natriuretic peptide (ANP) prohormone or a mimetic thereof adapted for infusion at a rate of about 1 to 400 ng per kg subject body weight per minute (ng/kg/min), for treating chronic congestive heart failure (CHF) or acute decompensated congestive heart failure (ADCHF) in a subject.

Alternatively, the present invention provides an infusion device containing, or provided with, a medicament comprising a peptide derived from atrial natriuretic peptide (ANP) prohormone or a mimetic thereof for treating chronic congestive heart failure (CHF) or acute decompensated congestive heart failure (ADCHF) in a subject, wherein said medicament is adapted to provide said subject with an effective amount of said peptide or mimetic of ≤4.5 µg/kg/day.

The infusion device may be selected from devices for intravenous (iv) infusion (eg a standard catheter, implantable drug port or iv drug infusion pump) or subcutaneous (sc) infusion (eg sc drug infusion pump).

The medicament, which may be as described above, may be contained within a reservoir provided within the device or which may otherwise be operably connected thereto. The arrangement of a connectable reservoir may be such that it is only capable of being reasonably used with the said device.

In one particularly preferred embodiment, the invention provides an infusion device containing, or provided with, a medicament comprising VSDL adapted for infusion at a rate of ≤50 ng/kg/min, for treating ADCHF in a subject.

In another particularly preferred embodiment, the invention provides an infusion device containing, or provided with, a medicament comprising VSDL adapted to provide said subject with an effective amount of said peptide or mimetic in the range of about 0.1 to 1.5 µg/kg/day, for treating ADCHF in a subject.

In a further aspect, the present invention provides the use of a peptide derived from atrial natriuretic peptide (ANP) prohormone or a mimetic thereof in the treatment of chronic congestive heart failure (CHF) or acute decompensated congestive heart failure (ADCHF) in a subject, characterised in that the peptide is infused into the subject at a rate of about 1 to 400 ng per kg subject body weight per minute (ng/kg/min).

In a still further aspect, the present invention provides the use of a peptide derived from atrial natriuretic peptide (ANP) prohormone or a mimetic thereof in the treatment of chronic congestive heart failure (CHF) or acute decompensated congestive heart failure (ADCHF) in a subject, characterised in that the peptide is administered into the subject at an effective amount of ≤4.5 µg/kg/day.

The present invention is hereinafter further described by way of the following, non-limiting example(s).

EXAMPLE(S)

Example 1

Treatment of ADCHF with iv Administration of Vessel Dilator

This example describes a study to examine whether VSDL administration to ADCHF patients will be safe and induce improvements in haemodynamic parameters, as well as renal, natriuretic and diuretic parameters, whilst regulating plasma volume and BP within clinically acceptable ranges and without seriously adverse side effects.

Methods and Materials

Formulation

VSDL in the form of a white lyophilised powder (synthesised using standard protein synthesis method by Auspep Pty Ltd, Parkville, VIC, Australia), stored in an ultra low freezer (−80° C.), was reconstituted in a vial with 10 ml of 0.9% saline (preservative free) and aseptically transferred into a 20 ml syringe (that connects to a patient cannula) before use.

Dosage

Initially, an iv dose of 12.5 ng/kg/min was infused into test subjects for 60 minutes with a syringe driver (Alaris Asena GS syringe driver; C are Fusion Corporation, San Diego, Calif., United States of America). This "safety dose" was chosen merely to trial the subjects for any adverse effects. Subsequently, a dose of 25 ng/kg/min (as infused for 60 minutes) was trialled. Additionally, a trial will be conducted with a dose of 50 ng/kg/min (for 60 minutes).

Study Population

Test adult subjects, both male and female, showing either acute exacerbations of chronic CHF or ADCHF (ie in individuals who had not previously shown heart failure), were recruited for the study. The following inclusion and exclusion criteria were applied:

Inclusion Criteria

In order to be eligible, a subject must have chronic CHF or ADCHF (NYHA class III—NYHA class IV) defined as:
1. Showing dyspnoea at rest or dyspnoea with minimal activity (ie difficulty breathing at rest while sitting, or difficulty breathing while lying flat or with one pillow, or difficulty breathing with minimal activity such as talking, eating); AND
2. Showing at least one of the following signs:
    Tachypnoea with respiratory rate >20 breaths per minute, OR
    Pulmonary congestion/oedema with rales or crackles/crepitations at least a third above lung bases; AND
3. At least one of the following objective measures:
    Showing, by chest X-ray, pulmonary oedema/congestions OR
    Circulating B-type natriuretic peptide (BNP) concentration of ≥400 pg/ml or circulating NT-proBNP concentration of ≥1000 pg/ml at presentation, OR
    PCWP >20 mmHg OR
    Showing systolic dysfunction within the last 12 months (EF<50%) as determined by TTE, nuclear testing, cardiac MRI or ventricular angiography); and be:
4. Male and/or female, 18 years or older; and
5. If a woman of child bearing potential, testing negative to 13-hCG.

Exclusion Criteria:
1. Evidence in the ED for Myocardial Infarction (MI) or high risk acute coronary syndrome within past 6 weeks, as determined by creatinine kinase (CK)/creatinine kinase muscle-brain isoenzyme (CK-MB) ≥2 times upper limit of normal or elevation of Troponin T at baseline >0.1 or as determined by Trans-Thoracic electrocardiogram (TTE);
2. Hypotension (SBP <90 mmHg), cardiogenic shock, volume depletion;
3. Persistent, uncontrolled hypertension (SBP >180 mm Hg);
4. Subjects with the presence of any CMR contra-indication (including PPM, cerebral aneurysm clips or non-MM approved metallic implant) are excluded from any MRI study component only;
5. Congenital heart defects (including Ventricular Septal Defect, Atrial Septal Defect, Patent Ductus Arteriosus, Tetralogy of Fallot, and Tricuspid Atresia);
6. Cardiac surgery within past 4 weeks;
7. Diastolic heart failure (preserved left ventricular function—determined by known history, ie E:E prime ratio>15);
8. Severe valvular heart disease: Aortic Stenosis <1.0 cm$^2$, any Idiopathic hypertrophic subaortic stenosis or Hypertrophic Obstructive Cardiomyopathy, acute Aortic Regurgitation grade 3 or 4 and Mitral Regurgitation grade 3 or 4;
9. History of cerebrovascular accident (within past 4 weeks) as determined by MM or Computerised Tomography (CT) Scan;
10. Acute or chronic active infection, including pneumonia and urinary tract infection documented by appropriate culture result;
11. Very significant renal impairment as determined by a creatinine clearance of <20 ml/min; and
12. Prior participation in any other clinical trial within past 30 days, including present day.

Three subjects were provided with a single dose of VSDL of 12.5 ng/kg/min for 60 minutes (ie single dose regimen) for a daily dose of 0.75 µg/kg. Subsequently, a further subject was trialled with a single dose of VSDL of 25 ng/kg/min for 60 minutes (to achieve a daily dosage of 1.5 µg/kg). Two further subjects are/have been recruited for trials with a single dose of VSDL of 25 ng/kg/min for 60 minutes, along with another subject (in a preliminary trial) for dosing with a single infusion of VSDL of 50 ng/kg/min for 60 minutes (to achieve a dosage of 3 µg/kg). The results will be compared with subjects recruited as a control group and who will receive a standard method of care for the treatment of ADCHF.

Assessment of Efficacy

Treated subjects were assessed by independent reviewers.

Markers of efficacy were measured at baseline (prior to VSDL infusion), 1 hour (post VSDL infusion), and 24 hours. The markers included CI, PCWP, pulmonary arterial wedge pressure (PAWP), BP, SVR and PVR, and were measured using standard methods well known to the person skilled in the art. Troponin T, proBNP, CK and CK-MB concentrations were also measured by standard methods.

Secondary efficacy variables that were measured included: dyspnea relief, and increased urine flow and volume output.

Results

Subjects Given 12.5 ng VSDL Per kg/min for 60 mins

The results shown by subjects treated with a single VSDL dose of 12.5 ng/kg/min for 60 mins are provided in FIGS. 1 and 2 and summarised in Table 1. The reviewers confirmed that they saw no safety risks.

Subjects Given 25 ng VSDL Per kg/min for 60 mins

The results shown by a subject treated with a single VSDL dose of 25 ng/kg/min for 60 mins are provided in Table 2. There were marked beneficial effects; in particular, decreasing dyspnea (ie from 3+ to 1+), increased CI, decreased systemic vascular resistance (SVR) and peripheral vascular resistance (PVR), and decreased PAWP. The infusion was well tolerated and no side effects were observed. The reviewers confirmed that they saw no safety risks.

TABLE 1

|  | Subject #1 | Subject #2 | Subject #3 |
|---|---|---|---|
| Summary of observations | This male subject received a single dose of iv VSDL in saline (12.5 ng/kg/min for 60 mins), on 28 Aug. 2010. The subject tolerated the infusion and was uncompromised during and post infusion. The subject responded during the infusion with an increase in cardiac index (CI), a drop in pulmonary capillary wedge pressure (PCWP), and an asymptomatic drop in blood pressure (BP). | This male subject received a single dose of iv VSDL in saline (12.5 ng/kg/min for 60 mins), on 1 Sep. 2010. The infusion was well tolerated by the subject. There was marked diuresis in the first 30 mins following infusion and dyspnea disappeared within 1 hour of starting infusion. There was no significant change in CI, PCWP or mean BP. However, SVR decreased 25% in the first 30 mins of the infusion; the VSDL therefore caused beneficial effects in the treatment of acute heart failure in this subject with global dyskinesis and no side-effects. The subject remained stable during the 24 hours following the infusion. | This female subject received a single dose of iv VSDL in saline (12.5 ng/kg/min for 60 mins), on 7 Oct. 2010. The subject tolerated the infusion well. There was an increase in CI, a fall in PCWP, and an asymptomatic drop in BP. It also appeared that SVR was improved. Further, the blood concentration of the CHF marker proBNP, decreased 75% during and within the 24 hours following the infusion. The subject also remained clinically stable during this period. |

TABLE 2

|  | Baseline | 24 hrs post-infusion |
|---|---|---|
| CI | 2.26 L/min/m² | 2.34 L/min/m² |
| PAWP | 22 mmHg | 6 mmHg |
| Arterial BP (mean) | 124 mmHg | 96 mmHg |
| Urinary Output |  | 2170 ml |
| Troponin T | <0.02 µg/L | <0.02 µg/L |
| CK | 188 U/L | 156 U/L |
| CK-MB | 2.0 µg/L | 1.3 µg/L |

Discussion

Since it was thought that subjects suffering significant CHF are unable to produce adequate endogenous amounts of natriuretic peptides to compensate for congestion, the present applicant had selected doses of exogenous VSDL infusion of 50 ng/kg/min, 100 ng/kg/min and 200 ng/kg/min for 60 minutes to ascertain the approximate amounts of exogenous VSDL required by late NHYA class III—NYHA class IV patients to reinstate homeostasis. Such doses were expected to result in an approximately 2-fold, 4-fold and 8-fold increase in total circulating VSDL, respectively. Further, the present applicant had particularly proposed an exogenous dose of VSDL at <100 ng/kg/min (for 60 mins) for the treatment of chronic CHF or ADCHF as a safe and effective dosage, since it has been identified that the release rate from the heart of VSDL with physiological stimuli is about 138 ng/kg body weight per minute[16] and similar dosages have been previously observed to cause a marked natriuresis and diuresis in healthy humans[17, 18] and, also, improved haemodynamic and renal parameters in persons with stable NYHA class III chronic CHF[10]. The molar equivalent of the 100 ng/kg body weight dose (for 60 mins) is 26 pmol/kg body weight (for 60 mins). However, in the preliminary trials described above, it was surprisingly found that beneficial effects for the treatment of chronic CHF can be achieved at doses that are much less than 100 ng/kg/min for 60 mins. In particular, at 12.5 ng/kg/min (for 60 mins) and 25 ng/kg/min (for 60 mins). One reviewer commented in respect of Subject #3 given 12.5 ng/kg/min (for 60 mins), that the observed 75% drop in the concentration of proBNP (a CHF marker) within 24 hours of the infusion was "truly spectacular".

Example 2

Estimation of Baseline and $C_{max}$ for VSDL following infusion

Following the surprising finding that beneficial effects for the treatment of chronic CHF can be achieved with doses that are much less than that which had been proposed, a study was undertaken to estimate the baseline levels of VSDL and $C_{max}$ (ie the peak VSDL concentration that is achieved) following infusion.

Methods and Materials $C_{max}$ was estimated from blood samples of a CHF patient (NYHA class III) taken at 30 mins, 1 hr, 1.5 hr, 2 hr, 3 hr, 4 hr, 5 hr, 6 hr and 12 hr following infusion, using a proprietary method (CPR Pharma Services Pty Ltd, Thebarton, SA, Australia) involving mass spectroscopy. The baseline VSDL concentration (ie endogenous level) was estimated from an identical sample taken prior to infusion (ie "predose").

Results

The baseline VSDL concentration was estimated as 0.024 ng/ml. The measured VSDL concentrations in the samples taken at the various time points are shown in Table 3 and FIG. 3. A corrected concentration, which accounts for the baseline concentration is also shown; however due to the low level of the baseline concentration, the corrected concentrations vary little from the actual, measured concentrations.

The $C_{max}$ was therefore 4.376 ng/ml (~4.4 ng/ml) achieved 30 mins (ie $T_{max}$ of 0.5 hr) after infusion. This value was also estimated after 1 hr. There is a slight curve to the measured VSDL concentration profile (FIG. 3) indicating that the elimination of VSDL from the blood stream does not clearly follow first order kinetics. Using the values shown in Table 3 to estimate the terminal elimination rate, the LOQ of 0.2 ng/ml gives an estimated half-life ($t_{1/2}$) of 20 minutes, while using the point just below the LOQ estimates a slightly longer half-life of 25-30 minutes, excluding and including the $C_{max}$ values, respectively.

TABLE 3

| Time point (hrs) | Corrected Concentration (ng/ml) | Concentration (ng/ml) |
|---|---|---|
| 0.5 | 4.376 | 4.4 |
| 1 | 4.376 | 4.4 |
| 1.5 | 1.176 | 1.2 |
| 2 | 0.556 | 0.58 |
| 3 | 0.136 | 0.16 |
| 4 | 0.061 | 0.085 |
| 5 | 0.022 | 0.046 |
| 6 | 0.005 | 0.029 |
| 12 | 0.018 | 0.042 |
| Predose | 0.024 | 0.024 |

Discussion

The baseline VSDL concentration in blood was estimated as 0.024 ng/ml. This was surprisingly low given previously published reports of endogenous basal levels of circulating VSDL in patients with varying degrees of CHF; for example, a basal VSDL concentration of 3412±546 (SEM) fmol/ml has been reported for CHF NYHA class III patients and 7691±1344 (SEM) fmol/ml for CHF NYHA class IV patients[6]. These values correspond to about 13.23 ng/ml and 29.82 ng/ml. $C_{max}$ for the infused VSDL was achieved at a $T_{max}$ of 0.5 hr. Further, the $t_{1/2}$ of 25-30 mins estimated from this study is much shorter than that previously reported (ie 120 mins). While not wishing to be bound by theory, it is considered that this previously reported $t_{1/2}$ of 120 mins may have been the result of inadvertently providing a supramaximal dose.

The surprising finding that effective treatment of chronic CHF or ADCHF patients with VSDL can be achieved with doses that are substantially lower than expected, is likely to have important implications in Chronic CHF and ADCHF treatment including, for example, avoidance of seriously adverse side effects as well as allowing treatment of patients with significant renal impairment (eg having a creatinine clearance of 20 to 60 ml/min) whom might otherwise may not have been regarded as treatable.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by the person skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

1. Heart Disease and Stroke Statistics-2003 update. Dallas: American Heart Association 2002.
2. Heywood J T, *Heart Fail Rev* 9:195-201 (2004).
3. Fonarow G, *Heart Fail Rev* 9:179-185 (2004).
4. Vesely D L, *Am J Physiology* 285:F167-F177 (2003).
5. Habibullah A A et al., *Clin Exp Pharmacol Physiol* 22:130-135 (1995).
6. Winters C J et al., *Circulation* 80:438-449 (1989).
7. Vesely D L et al., *Proc Soc Exp Biol Med* 192:230-235 (1989).
8. Hunter E F M et al., *Scan J Clin Lab Invest* 58:205-216 (1998).
9. Franz M et al., *Kidney Int* 58:374-378 (2000).
10. Vesely D L et al., *Circulation* 98:323-329 (1998).
11. Vesely D L et al., *Life Sci* 66(10):905-913 (2000).
12. De Palo E F et al., *Clin Chem* 46:843-847 (2000).
13. Franz M et al., *Kidney Int* 59:1928-1934 (2001).
14. Peacock W F and M D Emerman, *Heart Failure Reviews* 9:187-193 (2004).
15. Kirshenbaum K et al., *Curr Opin Struct Biol* 9:530-535 (1999).
16. Vesely D L et al., *J Clin Endocrinol Metab* 78:1128-1134 (1994).
17. Vesely D L et al., *Circulation* 90:1129-1140 (1994).
18. Vesely D L et al., *Peptides* 11:193-197 (1990).
19. Fonarow G C et al., *Arch Intern Med* 168(8):847-854 (2008).

The invention claimed is:

1. A method of treating acute decompensated congestive heart failure (ADCHF) in a subject, said method comprising administering to the subject an effective amount of vessel dilator (VSDL).

2. The method of claim 1, wherein the VSDL is administered by infusion at a rate of 1 to 400 ng per kg subject body weight per minute (ng/kg/min).

3. The method of claim 2, wherein the effective amount of the VSDL is in the range of 0.1 to 75 µg/kg/day.

4. The method of claim 1, wherein said effective amount is in the range of about 0.1 to 20 µg/kg/day and is administered by infusion at a rate of less than or equal to 50 ng/kg/min.

5. The method of claim 1, wherein said effective amount is in the range of about 0.1 to 1.5 µg/kg/day and is administered by infusion.

6. The method of claim 1, wherein the VSDL consists of the amino acid sequence shown as SEQ ID NO: 1.

* * * * *